United States Patent
Takeda et al.

(10) Patent No.: US 10,816,517 B2
(45) Date of Patent: Oct. 27, 2020

(54) METHOD FOR DETECTING TRIFLURIDINE-RELATED SUBSTANCE BY HIGH-PERFORMANCE LIQUID CHROMATOGRAPHY

(71) Applicant: TAIHO PHARMACEUTICAL CO., LTD., Chiyoda-ku (JP)

(72) Inventors: Daisuke Takeda, Tsukuba (JP); Akiyo Kojima, Tokushima (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 0 days.

(21) Appl. No.: 16/040,734

(22) Filed: Jul. 20, 2018

(65) Prior Publication Data

US 2019/0212309 A1    Jul. 11, 2019

(30) Foreign Application Priority Data

Jan. 5, 2018   (JP) ................................. 2018-000881

(51) Int. Cl.
G01N 30/36     (2006.01)
G01N 30/34     (2006.01)
(Continued)

(52) U.S. Cl.
CPC ............ *G01N 30/36* (2013.01); *G01N 30/34* (2013.01); *G01N 2030/027* (2013.01); *G01N 2030/8845* (2013.01)

(58) Field of Classification Search
None
See application file for complete search history.

(56) References Cited

U.S. PATENT DOCUMENTS

| 5,744,475 A | 4/1998 | Yano et al. |
| 6,159,969 A | 12/2000 | Yano et al. |

(Continued)

FOREIGN PATENT DOCUMENTS

| CN | 103788075 A | 5/2014 |
| CN | 105198947 A | 12/2015 |

(Continued)

OTHER PUBLICATIONS

Coulier, L. et al. "Simultaneous Quantitative Analysis of Metabolites Using Ion-Pair Liquid Chromatography-Electrospray Ionization Mass Spectrometry," Analytical Chemistry, vol. 78, No. 18, Sep. 15, 2006, 6573-6582. (Year: 2006).*

(Continued)

*Primary Examiner* — Christopher Adam Hixson
*Assistant Examiner* — Michelle Adams
(74) *Attorney, Agent, or Firm* — Oblon, McClelland, Maier & Neustadt, L.L.P.

(57) ABSTRACT

The present invention provides a novel method that is capable of detecting a trifluridine-related substance from a sample containing trifluridine or a salt thereof by high-performance liquid chromatography comprising two steps that are performed under gradient conditions. More specifically, the method is for detecting a trifluridine-related substance, the method comprising the step of subjecting a sample containing trifluridine or a salt thereof to high-performance liquid chromatography using a mobile phase composed of an organic phase and an aqueous phase, wherein the step of high-performance liquid chromatography comprises steps 1 and 2 that satisfy the following requirements: Step 1: the percentage of the organic phase in the entire mobile phase is 1 to 14% by volume; and Step 2: after step 1, elution is performed by applying a gradient of (Continued)

increasing the percentage of the organic phase in the entire mobile phase.

18 Claims, 3 Drawing Sheets

(51) Int. Cl.
GO1N 30/88 (2006.01)
GO1N 30/02 (2006.01)

(56) References Cited

U.S. PATENT DOCUMENTS

| | | | |
|---|---|---|---|
| 6,294,535 | B1 | 9/2001 | Yano et al. |
| 2007/0212763 | A1 | 9/2007 | Kai et al. |
| 2014/0356431 | A1 | 12/2014 | Ohnishi |
| 2014/0363512 | A1 | 12/2014 | Ohnishi et al. |
| 2017/0183039 | A1 | 6/2017 | Toyota et al. |
| 2019/0195840 | A1 | 6/2019 | Tokimitsu |
| 2019/0369063 | A1 | 12/2019 | Takeda et al. |

FOREIGN PATENT DOCUMENTS

| | | | |
|---|---|---|---|
| CN | 105461772 A | | 4/2016 |
| CN | 106220699 A | * | 12/2016 |
| CN | 106749194 A | | 5/2017 |
| CN | 103788075 B | | 3/2018 |
| CN | 108203437 A | | 6/2018 |
| EP | 1 849 470 A1 | | 10/2007 |
| JP | 60-56996 | | 4/1985 |
| JP | S60-56996 A | * | 4/1985 |
| JP | 61-010565 A | | 1/1986 |
| JP | 4437786 B2 | | 3/2010 |
| JP | 4441313 B2 | | 3/2010 |
| JP | 4603274 B2 | | 12/2010 |
| WO | WO 96/30346 A1 | | 10/1996 |
| WO | WO 2006/080327 A1 | | 8/2006 |
| WO | WO 2013/12213 A1 | | 8/2013 |
| WO | 2019/124544 A1 | | 6/2019 |
| WO | 2019/135405 A1 | | 7/2019 |

OTHER PUBLICATIONS

Nikitas, P. et al. "Multilinear gradient elution optimization in reversed-phase liquid chromatography based on logarithmic retention models: Application to separation of a set of purines, pyrimidines and nucleosides," Journal of Chromatography A, 1218 (2011) 5658-5663 (Year: 2011).*

Rammler, D.H. et al. "Studies on Polynucleotides. XVI. Specific Synthesis of the C3"-05" Interribonucleotidic Linkage. Examination of Routes Involving Protected Ribonucleosides and Ribonucleoside-3" Phosphates . . ." J. Am. Chem. Soc. 1962, 84, 16, 3112-3122. (Year: 1962).*

Horsch et al., "Influence of radiation sterilization on the stability of trifluorothymidine", International Journal of Pharmaceutics, 2001, vol. 222, pp. 205-215.

Moiseev et al., "Structure of Chemical Compounds, Methods of Analysis and Process Control", Pharmaceutical Chemistry Journal, 2007, vol. 41, No. 1, pp. 25-33.

Tanaka et al., "Repeated oral dosing of TAS-102 confers high trifluridine incorporation into DNA and sustained antitumor activity in mouse models", Oncology Reports, 2014, vol. 32, pp. 2319-2326.

Sakamoto et al., "Crucial roles of thymidine kinase 1 and deoxyUTPase in incorporating the antineoplastic nucleosides trifluridine and 2'-deoxy-5-fluorouridine into DNA", International Journal of Oncology, 2015, vol. 46, pp. 2327-2334.

Fresco-Taboada et al., "Development of an immobilized biocatalyst based on Bacillus psychrosaccharolyticus NDT for the preparative synthesis of trifluridine and decytabine", Catalysis Today, 2015, vol. 259, pp. 197-204.

Rizwan et al., "Analytical Method Development and Validation for the Simultaneous Determination of Tipiracil and Trifluridine in Bulk and Capsule Dosage Form by RP-HPLC Method", International Journal of Innovative Pharmaceutical Sciences and Research, 2017, vol. 5, No. 9, pp. 32-42.

Goday et al., "Development and Validation of Stability Indicating RP-HPLC Method for the Simultaneous Estimation of Combination Drugs Trifluridine and Tipiracil in Bulk and Pharmaceutical Dosage Forms", International Journal of Research in Applied, Natural and Social Sciences, 2017, vol. 5, Issue 2, pp. 93-103.

Jogi et al., "An Effective and Sensitive Stability Indicating Chromatographic Approach Based on RP-HPLC for Trifluridine and Tipiracil in Bulk and Pharmaceutical Dosage Form", International Journal of Research in Pharmacy and Chemistry, 2017, vol. 7, No. 1, pp. 63-70.

Paw et al., "Determination of trifluridine in eye drops by high-performance liquid chromatography", Pharmazie, 1997, vol. 52, No. 7, pp. 551-552.

Briggle et al., "Analysis of 5-Fluoro-2'-Deoxycytidine and 5-Trifluoromethyl-2'-Deoxycytidine and Their Related Antimetabolites by High-Performance Liquid Chromatography", Journal of Chromatography, 1986, vol. 381, pp. 343-355.

Riegel et al., "Determination of trifluorothymidine in the eye using high-performance liquid chromatography", Journal of Chromatography, 1991, vol. 568, pp. 467-474.

Balansard et al., "Determination of ophthalmic therapeutic trifluorothymidine and its degradation product by reversed-phase high-performance liquid chromatography", Journal of Chromatography, 1985, vol. 348, pp. 299-303.

Kawauchi et al., "Determination of a new thymidine phosphorylase inhibitor, TPI, in dog and rat plasma by reversed-phase ion-pair high-performance liquid chromatography", Journal of Chromatography B, 2001, vol. 751, pp. 325-330.

Lee et al., "Human mass balance study of TAS-102 using $^{14}$C analyzed by accelerator mass spectrometry", Cancer Chemother Pharmacol, 2016, vol. 77, pp. 515-526.

U.S. Appl. No. 15/952,367, filed Apr. 13, 2018, Yoshinori Tokimitsu.

U.S. Appl. No. 15/952,442, filed Apr. 13, 2018, Daisuke Takeda et al.

Tauraite et al., "Synthesis of novel derivatives of 5-carboxyuracil", CHEMIJA, 2015, vol. 26, No. 2, pp. 120-125.

Office Action dated Jan. 3, 2019, in co-pending U.S. Appl. No. 15/952,367.

Sahu et al., "Development and validation of a RP-HPLC-PDA method for simultaneous determination of trifluridine and tipiracil in pure and pharmaceutical dosageform", International Journal of Novel Trends in Pharmaceutical Sciences, vol. 7, No. 5. 2017. pp. 145-151.

Voorde et al., "Mycoplasma hyorhinis-encoded cytidine deaminase efficiently inactivates cytosine-based anticancer drugs", FEBS Open Bio, vol. 5, 2015, pp. 634-639.

Office Action dated Sep. 10, 2018, in co-pending U.S. Appl. No. 15/952,367.

Lee, M.G., "A High Pressure Liquid Chromatographic Method for the Determination of Trifluorothymidine Degradation in Aqueous Solution", International Journal of Pharmaceutics, 1980, vol. 5, pp. 19-24.

Haginoya, N. et al., "Nucleosides and Nucleotides. 160. Synthesis of Oligodeoxyribonucleotides Containing 5-(N-Aminoalkyl) carbamoyl-2'-deoxyuridines by a New Postsynthetic Modification Method and Their Thermal Stability and Nuclease-Resistance Properties", Bioconjugate Chemistry, 1997, vol. 8, No. 3, pp. 271-280.

Jones, M F., "The stability of trifluorothymidine: hydrolysis in buffered aqueous solutions", Journal of Pharmacy and Pharmacology, 1981, vol. 33, No. 5, pp. 274-278.

English Translation of International Search Report dated Mar. 26, 2019 in PCT/JP2018/047223, filed Dec. 21, 2018 (Original International Search Report in Japanese language was filed on Jun. 4, 2019).

English Translation of International Search Report dated Apr. 9, 2019 in PCT/JP2019/000010, filed Jan. 4, 2019 (Original International Search Report in Japanese language was filed on Jun. 4, 2019).

(56) References Cited

OTHER PUBLICATIONS

Rammler, et al., "Studies on Polynucleotides. XVI. Specific Synthesis of the $C_3$-$C_5$, Interribonucleotidic Linkage. Examination of Routes Involving Protected Ribonucleosides and Ribonucleoside-3' Phosphates. Syntheses of Uridylyl- (3'→5')-adenosine, Uridnyl-(3'→5')-cytidine, Adennyl-(3'→5')-adenosine and Related Compounds", J. Am. Chem. Soc., vol. 84, 1962, pp. 3112-3122.

Office Action dated Oct. 1, 2019 in co-pending U.S. Appl. No. 16/442,993.

Fukushima et al., "Structure and Activity of Specific Inhibitors of Thymidine Phosphorylase to Potentiate the Function of Antitumor 2'-Deoxyribonucleosides", Biochemical Pharmacology, vol. 59, pp. 1227-1236, 2000.

Hoff et al., "Phase I safety and pharmacokinetic study of oral TAS-102 once daily for fourteen days in patients with solid tumors", Proceedings of the 11th NCI AACR Symposium, pp. 13, 2000.

Dwivedy et al., "Safety and Pharmacokinetics (PK) of an Antitumor/Antiangiogenic Agent, TAs-102: a Phase I Study for Patients (PTS) with Solid Tumors", Proceedings of ASCO, vol. 20, pp. 18, 2001.

Thomas et al., "A dose-finding, safety and pharmacokinetics study of TAS-102, an antitumor/antiangiogenic agent given orally on a once-daily schedule for five days every three weeks in patients with solid tumors", Proceedings of the American Association for Cancer Research, vol. 43, pp. 21, 2002.

Shirasaka et al., "Preclinical and Clinical Practice of S-1 in Japan", Fluoropyrimidines in Cancer Therapy, pp. 285-302, 2004.

Emura et al., "An optimal dosing schedule for a novel combination antimetabolite, TAS-102, based on its intracellular metabolism and its incorporation into DNA", International Journal of Molecular Medicine, pp. 249-255, 2004.

\* cited by examiner

METHOD FOR DETECTING TRIFLURIDINE-RELATED SUBSTANCE BY HIGH-PERFORMANCE LIQUID CHROMATOGRAPHY

TECHNICAL FIELD

The present invention relates to a method for measuring a trifluridine-related substance contained in a pharmaceutical preparation containing trifluridine by high-performance liquid chromatography.

BACKGROUND ART

Related substances in medicinal drugs are generally measured by liquid chromatography, and a normal- or reversed-phase column system is commonly used with a mobile phase composed of a liquid mixture of water and an organic solvent. Trifluridine has long been used as an ophthalmic drop for infection treatment under the name of Viropic (registered trademark), and Lonsurf (registered trademark), a product of the Applicant, is a pharmaceutical preparation comprising trifluridine and tipiracil. The medicinal drug comprising trifluridine and tipiracil is sold as an antitumor agent, and there have been reports on this pharmaceutical preparation (Patent Literature (PTL) 1, PTL 2, PTL 3, and PTL 4).

Known trifluridine-related substances are 5-trifluoromethyluracil and 5-carboxyuracil, and Non-Patent Literature (NPL) 1 reports the use of high-performance liquid chromatography to measure these related substances.

NPL 2 reports that 5-trifluoromethyluracil, which is a trifluridine-related substance, can be measured by reversed-phase liquid chromatography under various conditions.

To measure the amount of trifluridine incorporated into tumor cells, NPL 3 reports using liquid chromatography.

To determine the substrate specificity of TK1 of trifluridine, NPL 4 reports using liquid chromatography.

To measure trifluridine in enzyme synthesis, NPL 5 reports using liquid chromatography.

Further, NPL 6, NPL 7, and NPL 8 report quantitative analysis of medicinal drugs that contain trifluridine and tipiracil by liquid chromatography.

To measure 5-trifluoromethyluracil, which is a trifluridine-related substance, NPL 2 reports various conditions for high-performance liquid chromatography using acetonitrile.

To measure the amount of trifluridine incorporated into tumor cells, NPL 3 reports conditions for high-performance liquid chromatography using acetonitrile.

To determine the substrate specificity of TK1 of trifluridine, NPL 4 reports conditions for high-performance liquid chromatography using acetonitrile.

To confirm trifluridine in enzyme synthesis, NPL 5 reports conditions for high-performance liquid chromatography with the use of trimethyl ammonium acetate in a gradient mode.

For quantitative measurement of trifluridine and tipiracil contained in Lonsurf, NPL 6, NPL 7, and NPL 8 report conditions for high-performance liquid chromatography using acetonitrile.

Regarding trifluridine as eye drops, NPL 9 and NPL 10 report conditions for high-performance liquid chromatography using methanol.

Regarding trifluridine, NPL 11, NPL 12, PTL 6, and PTL 13 report conditions for high-performance liquid chromatography using a mobile phase to which an acetate buffer, trifluoroacetic acid, or acetic acid is added.

Further, PTL 7 discloses performing high-performance liquid chromatography to confirm the purity of trifluridine; however, PTL 7 nowhere discloses conditions for the chromatography.

However, these reports nowhere suggest a method for detecting a trifluridine-related substance by high-performance liquid chromatography comprising two steps that are performed under gradient conditions.

CITATION LIST

Patent Literature

PTL 1: WO2013/122134
PTL 2: WO2013/122135
PTL 3: WO2006/080327
PTL 4: WO96/30346
PTL 5: CN106749194A
PTL 6: CN105198947A
PTL 7: CN105461772A
PTL 8: Japanese Patent No. 4603274
PTL 9: Japanese Patent No. 4441313
PTL 10: Japanese Patent No. 4437786

Non-Patent Literature

NPL 1: P. Horsch et al., International Journal of Pharmaceutics 222 (2001), pp. 205-215
NPL 2: D. V. Moiseev et al., Pharmaceutical Chemistry Journal 41, 1 (2007), pp. 25-33
NPL 3: N. TANAKA et al., Oncology Reports 32 (2014), pp. 2319-2326
NPL 4: K. SAKAMOTO et al., International Journal of Oncology 46 (2015), pp. 2327-2334
NPL 5: A. Fresco-Taboada et al., Catalysis Today 259 (2015), pp. 197-204
NPL 6: M. S. H. Rizwan et al., International Journal of Innovative Pharmaceutical Sciences and Research 5 (2017), pp. 32-42
NPL 7: S. GODAY et al., International Journal of Research in Applied, Natural and Social Sciences 5 (2017), pp. 93-104
NPL 8: K. Jogi et al., International Journal of Research in Pharmacy and Chemistry 7 (2017), pp. 63-70
NPL 9: B. Paw et al., Pharmazie 7 (1997), pp. 551-552
NPL 10: T. Briggle et al., Journal of Chromatography 381 (1986), pp. 343-355
NPL 11: M. Riegel et al., Journal of Chromatography 568 (1991), pp. 467-474
NPL 12: G. Balansard et al., Journal of Chromatography 348 (1985), pp. 299-303
NPL 13: T. Kawauchi et al., Journal of Chromatography 751 (2001), pp. 325-330

SUMMARY OF INVENTION

Technical Problem

The problem to be solved by the present invention is to provide a novel method that is capable of detecting a trifluridine-related substance from a sample containing trifluridine or a salt thereof by high-performance liquid chromatography comprising two steps that are performed under gradient conditions.

Solution to Problem

The present inventors conducted extensive research and found a method that is capable of efficiently detecting related substances of trifluridine or a salt thereof by high-performance liquid chromatography under specific conditions, and found that the method is suitable for assuring the quality thereof.

Therefore, the present invention provides the following Items 1 to 16.

1. A method for detecting a trifluridine-related substance, the method comprising the step of subjecting a sample containing trifluridine or a salt thereof to high-performance liquid chromatography using a mobile phase composed of an organic phase and an aqueous phase, wherein the step of high-performance liquid chromatography comprises steps 1 and 2 that satisfy the following requirements:
Step 1: the percentage of the organic phase in the entire mobile phase is 1 to 14% by volume; and
Step 2: after step 1, elution is performed by applying a gradient of increasing the percentage of the organic phase in the entire mobile phase.

2. The method according to Item 1, wherein the related substance is at least one member selected from the group consisting of the following related substances 1 to 6:
related substance 1: 5-carboxyuracil,
related substance 2: 5-carboxy-2'-deoxy-uridine,
related substance 3: 2'-deoxy-5-methoxycarbonyluridine,
related substance 4: trifluorothymine,
related substance 5: 5-methoxycarbonyluracil, and
related substance 6: 5'-(4-chlorophenylcarboxy)-2'-deoxy-5-trifluoromethyluridine.

3. The method according to Item 1 or 2, wherein related substances 1 to 5 are detected in step 1, and related substance 6 is detected in step 2.

4. The method according to any one of Items 1 to 3, wherein step 1 is performed under isocratic conditions.

5. The method according to any one of Items 1 to 4, wherein the organic phase is acetonitrile.

6. The method according to any one of Items 1 to 5, wherein, in step 1, the percentage of the organic phase in the entire mobile phase is within a range of 2 to 10% by volume.

7. The method according to any one of Items 1 to 6, wherein the percentage of the organic phase in the entire mobile phase at the end of step 2 is within a range of 25 to 70% by volume.

8. The method according to any one of Items 1 to 7, wherein, in step 2, the elution is performed by applying a gradient of increasing the percentage of the organic phase in the entire mobile phase by 0.9% by volume or more per 1 minute.

9. The method according to any one of Items 1 to 8, wherein the measurement time in step 2 is within a range of 10 to 50 minutes.

10. The method according to any one of Items 1 to 9, wherein the flow rate at the end of step 2 is 1.0 to 1.5 times the flow rate in step 1.

11. The method according to any one of Items 1 to 10, wherein the aqueous phase further contains phosphate.

12. The method according to any one of Items 1 to 11, wherein the aqueous phase further contains methanol.

13. 5-Carboxy-2'-deoxy-uridine (related substance 2) for use in quality control of a combination drug containing trifluridine or a salt thereof.

14. 5-Carboxy-2'-deoxy-uridine (related substance 2) for use as a standard for detecting impurities in a combination drug containing trifluridine or a salt thereof.

15. 2'-Deoxy-5-methoxycarbonyluridine (related substance 3) for use in quality control of a combination drug containing trifluridine or a salt thereof.

16. 2'-Deoxy-5-methoxycarbonyluridine (related substance 3) for use as a standard for detecting impurities in a combination drug containing trifluridine or a salt thereof.

17. 5-Methoxycarbonyluracil (related substance 5) for use in quality control of a combination drug containing trifluridine or a salt thereof.

18. 5-Methoxycarbonyluracil (related substance 5) for use as a standard for detecting impurities in a combination drug containing trifluridine or a salt thereof.

19. 5'-(4-Chlorophenylcarboxy)-2'-deoxy-5-trifluoromethyluridine (related substance 6) for use in quality control of a combination drug containing trifluridine or a salt thereof.

20. 5'-(4-Chlorophenylcarboxy-2'-deoxy-5-trifluoromethyluridine (related substance 6) for use as a standard for detecting impurities in a combination drug containing trifluridine or a salt thereof.

Advantageous Effects of Invention

According to the method of the present invention, related substances of trifluridine or a salt thereof can be efficiently detected by high-performance liquid chromatography using a mobile phase composed of an organic phase and an aqueous phase. Further, the method of the present invention is suitable for assuring the quality thereof.

DESCRIPTION OF EMBODIMENTS

Figure 1:
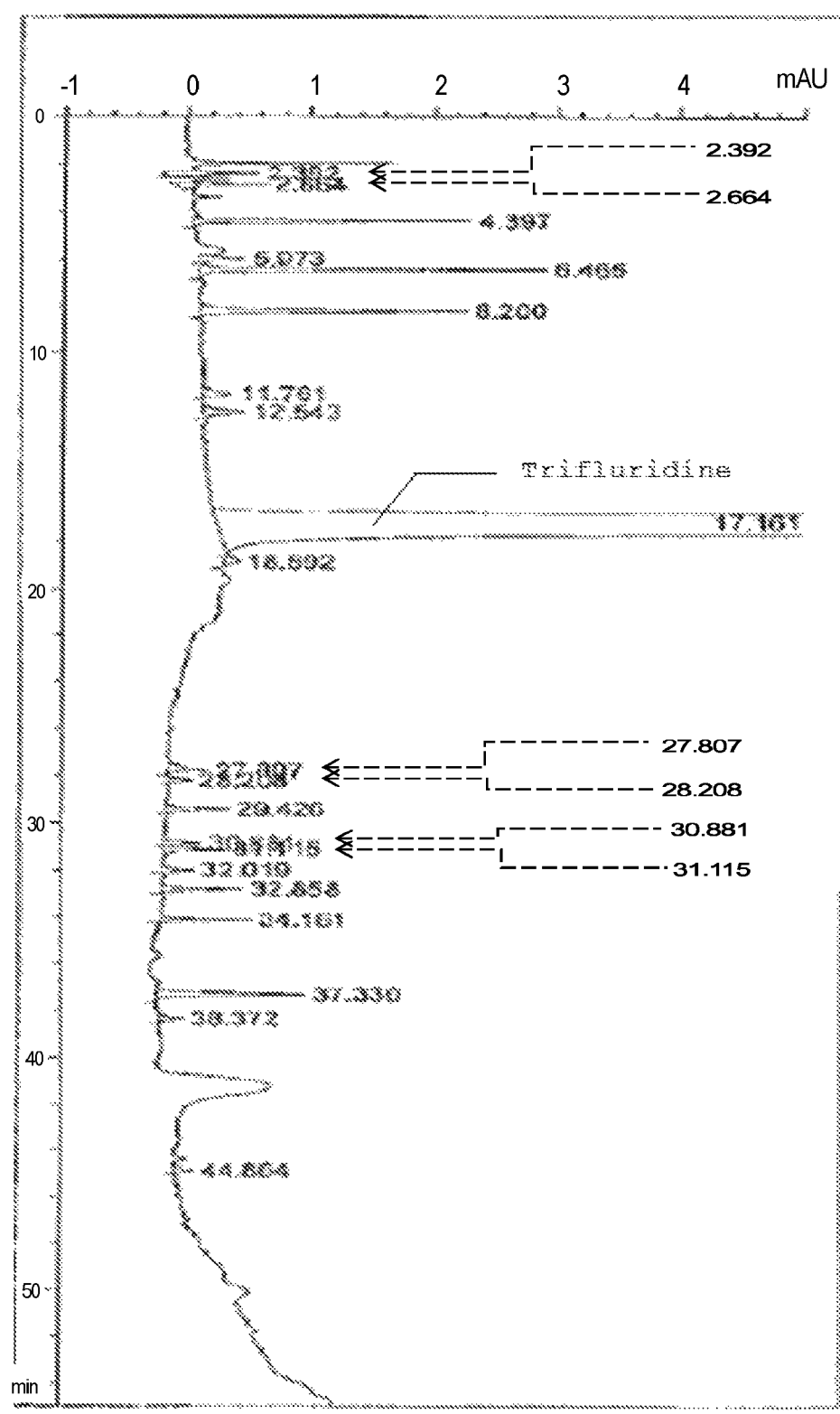
FIG. 1 shows the chromatogram obtained in Example 1-1.

Trifluridine (FTD) referred to in the present invention is α,α,α,-trifluorothymidine and is a compound having the following structure:

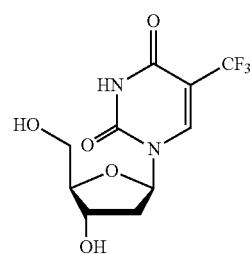

In the present invention, when trifluridine has isomers, such as optical isomers, stereoisomers, rotational isomers, and tautomers, all of the isomers and mixtures thereof are encompassed within the scope of the compound of the present invention, unless otherwise stated.

In the present invention, a salt refers to a pharmaceutically acceptable salt, unless otherwise stated, and may be a base addition salt or an acid addition salt.

Examples of base addition salts include alkali metal salts, such as sodium salts and potassium salts; alkaline earth metal salts, such as calcium salts and magnesium salts; ammonium salts; and organic amine salts, such as trimethylamine salts, triethylamine salts, dicyclohexylamine salts, ethanolamine salts, diethanolamine salts, triethanolamine salts, procaine salts, and N,N'-dibenzylethylenediamine salts.

Examples of acid addition salts include inorganic acid salts, such as hydrochloride, sulfate, nitrate, phosphate, and perchlorate; organic acid salts, such as acetate, formate, maleate, fumarate, tartrate, citrate, ascorbate, and trifluoroacetate; and sulfonates, such as methanesulfonate, isethionate, benzenesulfonate, and p-toluenesulfonate.

The trifluridine or a salt thereof used in the present invention is preferably trifluridine in the free, non-salt foLnL.

The method of the present invention is capable of detecting a trifluridine-related substance by preparing a sample containing a solvent and trifluridine or a salt thereof, and subjecting the sample to high-performance liquid chromatography.

The sample according to the present invention can contain a trifluridine-related substance. Examples of the related substances include the compounds shown as related substances 1 to 6.

TABLE 1

| Related Substance | Compound Name | Structural Formula |
|---|---|---|
| 1 | 5-Carboxyuracil | |
| 2 | 5-Carboxy-2'-deoxyuridine | |
| 3 | 2'-Deoxy-5-methoxycarbonyluridine | |
| 4 | Trifluorothymine | |
| 5 | 5-Methoxycarbonyluracil | |
| 6 | 5'-(4-Chlorophenylcarboxy-2'-deoxy-5-trifluoromethyluridine) | |

Related substance 1 is 5-carboxyuracil. Related substance 1 may be sometimes referred to as 2,4-dioxo-1,2,3,4-tetrahydropyrimidine-5-carboxylic acid.

Related substance 2 is 5-carboxy-2'-deoxy-uridine. Related substance 2 may be sometimes referred to as 1-((2R,4R,5R)-4-hydroxy-5-(hydroxymethyl)tetrahydrofuran-2-yl)-2,4-dioxo-1,2,3,4-tetrahydropyrimidine-5-carboxylic acid.

Related substance 3 is 2'-deoxy-5-methoxycarbonyluridine. Related substance 3 may be sometimes referred to as 1-((2R,4R,5R)-4-hydroxy-5-(hydroxymethyl)tetrahydrofuran-2-yl)-2,4-dioxo-1,2,3,4-tetrahydropyrimidine-5-methyl carboxylic acid.

Related substance 4 is trifluorothymine. Related substance 4 may be sometimes referred to as 5-(trifluoromethyl)pyrimidine-2,4(1H,3H)-dione.

Related substance 5 is 5-methoxycarbonyluracil. Related substance 5 may be sometimes referred to as 2,4-dioxo-1,2,3,4-tetrahydropyrimidine-5-methyl carboxylic acid.

Related substance 6 is 5'-(4-chlorophenylcarboxy-2'-deoxy-5-trifluoromethyluridine). Related substance 6 may be sometimes referred to as ((2R,3R,5R)-5-(2,4-dioxo-5-(trifluoromethyl)-3,4-dihydropyrimidin-1(2H)-yl)-3-hydroxytetrahydrofuran-2-yl)methyl 4-chlorobenzoate.

In addition to samples prepared from a pharmaceutical preparation or drug substance itself, it is possible in the present invention to use samples prepared in a test for determining stability etc., samples prepared by adding each related substance to study the retention time etc. of the related substance, samples prepared to confirm the manufacturing process of a pharmaceutical preparation or drug substance, and the like. The sample may contain or may not substantially contain tipiracil or a salt thereof contained in Lonsurf (registered trademark).

The pharmaceutical preparation usable in the present invention contains trifluridine or a salt thereof and optionally a pharmaceutically acceptable carrier, and may be formed into a suitable dosage form according to prevention and treatment purposes. Examples of the dosage form include oral preparations, ophthalmic solutions, injections, suppositories, ointments, patches, and the like, with oral preparations being preferable. Such dosage forms can be formed by methods conventionally known to persons skilled in the art.

As the pharmaceutically acceptable carrier, various conventional organic or inorganic carrier materials used as preparation materials may be incorporated as an excipient, binder, disintegrant, lubricant, or colorant in solid preparations; or as a solvent, solubilizing agent, suspending agent, isotonizing agent, buffer, or soothing agent in liquid preparations. It is also possible to use pharmaceutical preparation additives, such as antiseptics, antioxidants, colorants, sweeteners, and stabilizers, if required.

Oral solid preparations when prepared are produced by adding an excipient and optionally a binder, disintegrant, lubricant, colorant, taste-masking or flavoring agent, etc., to trifluridine or a salt thereof, and formulating the resulting mixture into tablets, coated tablets, granules, powders, capsules, or the like by ordinary methods.

Ophthalmic solutions when prepared are produced by using trifluridine or a salt thereof with a solubilizing agent, an isotonizing agent, a buffer, an antiseptic, and the like.

The daily dose of the medicinal drug in such a dosage form may be suitably determined according to the condition, body weight, age, gender, etc., of the patient.

To perform high-performance liquid chromatography in the present invention, a commercially available chromatography device can be used.

Known columns for chromatography include normal-phase columns, in which an organic phase is used as the mobile phase to separate lipophilic compounds, and reversed-phase columns, in which an aqueous phase is used as the mobile phase to separate compounds. In high-performance liquid chromatography, a reversed-phase column is often used. In the present invention as well, reversed-phase chromatography is preferable.

The column for high-performance liquid chromatography usable in the present invention is selected from a silica gel column, a column containing silica gel whose surface is modified with octadecyl silyl groups (an ODS column or C18 column), a column containing silica gel whose surface is modified with octyl groups (a C8 column), a column containing silica gel whose surface is modified with cyanopropyl groups (a CN column), a column containing silica gel whose surface is modified with phenethyl groups (a Ph column), a column containing silica gel whose surface is modified with aminopropyl groups (an NH column), a column containing silica gel whose surface is modified with dihydroxypropyl groups (a Diol column), a column packed with various polymers (a polymer column), a column packed with ion-exchange resin (an ion-exchange column), and the like. In the present invention, an ODS column is preferable.

It is possible to use various types of ODS columns with different silica gel particle sizes, different pore sizes, different types of bonding of octadecyl silyl groups, different degrees of substitution of octadecyl silyl groups, etc. In the present invention, a high-purity silica gel is used, and it is preferable to use an ODS column (an end-capped ODS column) in which residual silanol obtained after octadecylation is treated with a low-molecular-weight silylating agent.

It is possible to use various types of ODS columns with different silica gel particle sizes, different pore sizes, different types of bonding of octadecyl silyl groups, different degrees of substitution of octadecyl silyl groups, etc. In the present invention, the silica gel preferably has an average particle size of, for example, 2 to 10 μm, and more preferably 3 to 5 μm. The average particle size of silica gel can be measured by, for example, laser diffractometry. The silica gel has an average pore size of, for example, 6 to 20 nm, and more preferably 8 to 13 nm. The average pore size of silica gel can be measured by a gas absorption method etc. The bonding type of octadecyl silyl groups in the silica gel is preferably, for example, monomeric or polymeric. The degree of substitution of octadecyl silyl groups can be measured by various methods. The carbon content in the silica gel is preferably, for example, 3% or more, and more preferably 10% or more. The carbon content in the silica gel is preferably, for example, 25% or less, and more preferably 20% or less. The carbon content in the silica gel can be measured by various methods.

Examples of the organic phase used in the mobile phase in high-performance liquid chromatography include nonpolar solvents, such as hexane, cyclohexane, heptane, diethyl ether, tetrahydrofuran, chloroform, and methylene chloride; aprotic polar solvents, such as acetone, dimethylsulfoxide, and acetonitrile; acetic acid; methanol; ethanol; isopropanol; acetonitrile; and the like. These solvents may be used alone, or two or more of these solvents may be used as a mixed solvent. The organic phase according to the present invention is preferably methanol or acetonitrile, and more preferably acetonitrile. The organic phase may contain 10% or less of water.

The aqueous phase used in the mobile phase in high-performance liquid chromatography may contain 10% or less of an organic solvent in addition to water. The aqueous phase preferably contains 10% or less of methanol, more preferably 5% or less of methanol, still more preferably 2% or less of methanol, and particularly preferably 0.1 to 1% of methanol, in the entire aqueous phase.

To enable reproducibility, various buffers can be added to the mobile phase in high-performance liquid chromatography. For example, it is possible to add acetic acid or a salt thereof, citric acid or a salt thereof, tartaric acid or a salt thereof, and phosphoric acid or a salt thereof. Examples of acetic acid or a salt thereof include acetic acid and sodium acetate. Examples of citric acid or a salt thereof include citric acid, monosodium citrate, disodium citrate, and trisodium citrate. Examples of tartaric acid or a salt thereof include tartaric acid and sodium tartrate. Examples of phosphoric acid or a salt thereof include phosphoric acid, sodium dihydrogenphosphate, disodium hydrogenphosphate, potassium dihydrogen phosphate, and dipotassium hydrogen phosphate. Additives in the aqueous phase according to the present invention are preferably phosphate, and more preferably sodium dihydrogenphosphate, from the viewpoint of the properties of the substances to be measured, the shape of the peaks obtained by the measurement, as well as the measurement reproducibility. These additives may be used alone or in a combination of two or more.

The concentration of the buffer that can be used in the present invention may be suitably adjusted within a concentration range in which the buffer does not undergo precipitation during the high-performance liquid chromatography measurement. The concentration is preferably 1 to 50 mM, more preferably 5 to 40 mM, still more preferably 10 to 30 mM, and particularly preferably 18 to 20 mM.

For high-performance liquid chromatography, a mixture of an organic phase and an aqueous phase is used as the mobile phase. In the present invention, the percentage of the organic phase in the entire mobile phase is preferably within a range of 1 to 14% by volume, more preferably 2 to 10% by volume, and particularly preferably 3 to 7% by volume at the retention times of related substances 1, 2, 3, 4, and 5, and trifluridine.

As the mobile phase in high-performance liquid chromatography, a mixture of an organic phase and an aqueous phase is used. The ratio thereof is often made to vary during the measurement, and this is referred to as a gradient application.

The gradient application is usually performed often in consideration of the retention time of the target compound and the separation of the target compound and related substances from each other.

The present invention is characterized by gradient conditions of steps 1 and 2.

Step 1: The percentage of the organic phase in the entire mobile phase is 1 to 14% by volume.

Step 2: After step 1, elution is performed by applying a gradient of further increasing the percentage of the organic phase in the entire mobile phase.

In step 1, the mobile phase may be used in a gradient or isocratic mode, and is preferably used in an isocratic mode. Further, in step 1, the percentage of the organic phase in the entire mobile phase may be, for example, 1 to 14% by volume, more preferably 2 to 10% by volume, and particularly preferably 3 to 7% by volume. In the present invention, the phrase "in step 1, the percentage of the organic phase in the entire mobile phase is X to Y % by volume" means that the percentage thereof is within a range of X to Y % by volume during step 1.

Step 1 is initiated within 5 minutes of, preferably within 3 minutes of, more preferably within 1 minute of, and particularly preferably simultaneously with, the injection of the sample into the high-performance liquid chromatography.

Step 1 is completed 13 to 30 minutes after the sample is injected into the high-performance liquid chromatography. Step 1 is preferably completed 15 to 28 minutes and preferably 17 to 25 minutes after the injection, so that trifluridine does not overlap with valleys or ghost peaks in the baseline.

The measurement time in step 1 is not particularly limited as long as it is within the range between the initiation and completion stated above. The measurement time is preferably 15 to 28 minutes, and more preferably 17 to 25 minutes.

The upper limit of the flow rate of the mobile phase in step 1 is not limited as long as it is commonly applied to high-performance liquid chromatography. In consideration of the separation of the retention time of each related substance, the flow rate is preferably 2.5 mL/min or less, more preferably 2.0 mL/min or less, still more preferably 1.5 mL/min or less, yet more preferably 1.3 mL/min or less, and particularly preferably 1.1 mL/min or less. The range of the flow rate of the mobile phase in step 1 is not particularly limited. For example, it is preferably 0.5 to 2.5 mL/min, more preferably 0.5 to 2.0 mL/min, still more preferably 0.7 to 1.5 mL/min, yet more preferably 0.8 to 1.3 mL/min, and particularly preferably 0.9 to 1.1 mL/min.

In this manner, in step 1, at least one trifluridine-related substance selected from the group consisting of related substances 1, 2, 3, 4, and 5 can be detected. In step 1, it is preferable that related substances 1, 2, 3, 4, and 5 be detected.

From the viewpoint of performing step 1 under more isocratic conditions, when at least one member from among related substances 1, 2, 3, 4, and 5 is detected in step 1, the difference between the maximum value and the minimum value of the percentage of the organic phase in the entire mobile phase is preferably 5% by volume or less, and particularly preferably 1% by volume or less, with respect to the entire mobile phase at the retention time of each substance detected in step 1 from among related substances 1, 2, 3, 4, and 5.

In step 2, the percentage of the organic phase is increased with a mobile-phase gradient. If step 1 is performed under gradient conditions, then a gradient is applied in step 2 so as to further increase the percentage of the organic phase. If step 1 is performed under isocratic conditions, then a gradient is applied in step 2 to increase the percentage of the organic phase.

The percentage of the organic phase in the entire mobile phase at the end of step 2 is 25 to 70% by volume, more preferably 30 to 65% by volume, and particularly preferably 35 to 60% by volume. In the present invention, the phrase "at the end of step 2" refers to the time at which the gradient application is stopped so that the percentage of the organic phase in the entire mobile phase starts to decrease in step 2.

When to start step 2 is not particularly limited as long as step 2 is started within 3 minutes after the completion of step 1. Step 2 is preferably started within 1 minute after, and preferably simultaneously with, the completion of step 1.

The completion of step 2 is not particularly limited as long as it is after the retention time of related substance 6. Step 2 is preferably completed 35 to 65 minutes, and preferably 40 to 60 minutes after the injection of the sample into the high-performance liquid chromatography.

The measurement time in step 2 is not particularly limited as long as the retention time of related substance 6 can be measured, and is preferably 10 to 50 minutes, and more preferably 15 to 45 minutes.

The gradient in step 2 is not particularly limited as long as the percentage of the organic phase in the entire mobile phase is increased. The percentage of the organic phase in the entire mobile phase is preferably increased by 0.9% by volume or more per 1 minute, more preferably increased by 1.0% by volume or more per 1 minute, and particularly preferably increased by 2.0% by volume or more per 1 minute. The upper limit of the increase in the percentage of the organic phase in the entire mobile phase is not particularly limited, and is preferably, for example, 10% by volume or less per 1 minute, and more preferably, for example, 5.0% by volume or less per 1 minute. In this specification, when the percentage of the organic phase in the entire mobile phase is increased by X % by volume per unit time (e.g., per 1 minute), the percentage of the organic phase in the entire mobile phase is increased by X % by volume with respect to 100% by volume of the entire mobile phase per unit time. Further, in the present invention, the change in the percentage of the organic phase in the entire mobile phase during the measurement in step 2 (the difference between the maximum value and the minimum value of the percentage of the organic phase in the entire mobile phase during the measurement) is preferably 30% by volume or more, and particularly preferably 50% by volume or more, with respect to the entire mobile phase. The upper limit of the change in the percentage of the organic phase in the entire mobile phase during the measurement in step 2 is not particularly limited, and is preferably, for example, 80% by volume or less, and particularly preferably 70% by volume or less, with respect to the entire mobile phase.

The flow rate of the mobile phase in step 2 is not limited as long as it is commonly applied to high-performance liquid chromatography. In consideration of the separation of the retention time of each related substance, the flow rate is preferably 2.5 mL/min or less, more preferably 2.0 mL/min or less, and still more preferably 1.5 mL/min or less. The range of the flow rate of the mobile phase in step 2 is not particularly limited, and is, for example, preferably 0.5 to 2.5 mL/min, more preferably 0.5 to 2.0 mL/min, and still more preferably 1.0 to 1.5 mL/min. To shorten the entire measurement time, it is possible to gradually increase the flow rate after the initiation of step 2. The flow rate at the end of step 2 is preferably 1.0 to 1.5 times the flow rate at the end of step 1.

In this manner, in step 2, related substance 6 can be detected.

In the present invention, it is possible to add an ion-pair reagent, in addition to the additives above. Examples of usable ion-pair reagents include sodium alkylsulfonates, such as sodium pentanesulfonate, sodium hexanesulfonate, sodium heptanesulfonate, sodium octanesulfonate, and sodium dodecanesulfonate; sodium alkylsulfates, such as sodium dodecyl sulfate; quaternary ammonium salts, such as tetraethyl ammonium hydroxide, tetrabutyl ammonium hydroxide, tetrabutyl ammonium chloride, and tetrabutyl ammonium bromide; and tertiary amines, such as trihexylamine and trioctylamine.

The pH of the mobile phase (typically the aqueous phase) according to the present invention can be suitably adjusted with the addition of the additives mentioned above, and is preferably 2.0 to 5.0.

The detection wavelength usable in the present invention may be 208 to 280 nm, preferably 208 to 240 nm, and more preferably 208 to 212 nm, in consideration of the properties of each related substance.

The temperature of the mobile phase in the column used in the method of the present invention may be suitably set. In consideration of the effect from the external environment, reproducibility, and the like, the temperature is preferably maintained constant, and is more preferably 25 to 50° C., still more preferably 35 to 45° C., and particularly preferably 40 to 44° C. To maintain the temperature constant, the temperature of the entire column is controlled, and in addition, a preheated mixer or the like can be used.

In the high-performance liquid chromatography according to the present invention, the injection amount, the temperature within the column, etc., may be suitably changed.

Of these related substances, related substances 1 to 5 may be synthesized by known methods or may be obtained from commercially available products. Related substance 6 may be synthesized from trifluridine or commercially available compounds by using known methods or may be obtained by the method described later. Related substances can be identified by comparing the retention times in high-performance liquid chromatography, mass spectra, and results from a photodiode array (PDA) between the thus-obtained related substances and the related substances detected in accordance with the present invention.

Further, these related substances can be quantitatively measured by either an external standard method or internal standard method.

When these related substances are possibly contained as impurities in a medicinal drug or pharmaceutical preparation, these related substances are regulated in accordance with guideline ICH-Q3A of the International Council for Harmonisation of Technical Requirements for Pharmaceuticals for Human Use. The method of the present invention is very useful since it is possible to confirm whether the standard of the guideline is satisfied.

Further, these related substances can be detected from trifluridine or a salt thereof using the method of the present invention. Further yet, in the present invention, at least one substance selected from related substances 1 to 6, preferably three or more substances selected from related substances 1 to 6, more preferably four or more substances selected from related substances 1 to 6, and particularly preferably related substances 2, 3, 5, and 6, can be used as a standard of quality control.

Trifluridine and trifluridine-related substances used as a standard are of high purity; therefore, the related substances separated under the conditions described above for high-performance liquid chromatography can be used as a standard. That is, the present invention may also be referred to as a method for producing the related substances, the method comprising separating the related substances from a combination drug containing trifluridine or a salt thereof. These related substances may be related substances 1 to 6 mentioned above, with related substances 2, 3, 5, and 6 being preferable.

In the present invention, it is unknown that trifluridine includes related substance 2, 3, 5 or 6, and in particular, related substance 6 is a novel substance. Therefore, the present invention encompasses related substance 2, 3, 5, or 6 used for quality control of a pharmaceutical composition containing trifluridine or a salt thereof, and further encompasses related substance 2, 3, 5, or 6 for use as a standard for detecting impurities in a pharmaceutical composition containing trifluridine or a salt thereof. Additionally, the present invention also encompasses a method for producing related substance 2, 3, 5, or 6, the method comprising separating the related substances and a pharmaceutical composition containing trifluridine or a salt thereof from each other.

In the present invention, a method of high-performance liquid chromatography is used to detect trifluridine-related substances.

The method is preferably for detecting at least one trifluridine-related substance selected from the group consisting of related substances 1 to 6 and satisfies the following requirements in steps 1 and 2:
Step 1: the percentage of the organic phase in the entire mobile phase is 1 to 14% by volume.
Step 2: after step 1, elution is performed by applying a gradient of further increasing the percentage of the organic phase.

The method more preferably satisfies the following requirements in steps 1 and 2:
Step 1: at least one trifluridine-related substance selected from the group consisting of related substances 1 to 5 is detected, the percentage of the organic phase in the entire mobile phase is 1 to 14% by volume, and the operation mode is isocratic.
Step 2: after step 1, elution is performed by applying a gradient of further increasing the percentage of the organic phase, and related substance 6 is detected.

The method more preferably satisfies the following requirements in steps 1 and 2:
Step 1: the percentage of the organic phase in the entire mobile phase is 2 to 10% by volume, the operation mode is isocratic, and related substances 1 to 5 are detected.
Step 2: after step 1, elution is performed by applying a gradient of further increasing the percentage of the organic phase, and related substance 6 is detected.

The method more preferably satisfies the following requirements in steps 1 and 2, wherein the organic phase in the mobile phase contains acetonitrile:
Step 1: the percentage of the organic phase in the entire mobile phase is 2 to 10% by volume, the operation mode is isocratic, and related substances 1 to 5 are detected.
Step 2: after step 1, elution is performed by applying a gradient of further increasing the percentage of the organic phase, the percentage of the organic phase in the entire mobile phase at the end of step 2 is 25 to 70% by volume, and related substance 6 is detected.

The method more preferably satisfies the following requirements in steps 1 and 2, wherein the organic phase in the mobile phase contains acetonitrile, the aqueous phase contains water, and the mobile phase contains phosphate:
Step 1: the percentage of the organic phase in the entire mobile phase is 2 to 10% by volume, the operation mode is isocratic, and related substances 1 to 5 are detected.
Step 2: after step 1, elution is performed by applying a gradient of increasing the percentage of the organic phase by 0.9% by volume or more per 1 minute, the percentage of the organic phase in the entire mobile phase at the end of step 2 is 30 to 65% by volume, and related substance 6 is detected.

The method more preferably satisfies the following requirements in steps 1 and 2, wherein the organic phase in the mobile phase contains acetonitrile, the aqueous phase contains water, and the mobile phase contains phosphate:
Step 1: the percentage of the organic phase in the entire mobile phase is 2 to 10% by volume, the operation mode is isocratic, and related substances 1 to 5 are detected.
Step 2: after step 1, elution is performed by applying a gradient of increasing the percentage of the organic phase in the entire mobile phase by 0.9% by volume or more per 1 minute, the percentage of the organic phase in the entire mobile phase at the end of step 2 is 30 to 65% by volume, and related substance 6 is detected.

The method more preferably satisfies the following requirements in steps 1 and 2, wherein the organic phase in the mobile phase contains acetonitrile, the aqueous phase contains water, and the mobile phase contains phosphate:
Step 1: the percentage of the organic phase in the entire mobile phase is 3 to 7% by volume, the operation mode is isocratic, and related substances 1 to 5 are detected.
Step 2: after step 1, elution is performed by applying a gradient of increasing the percentage of the organic phase in the entire mobile phase by 0.9% by volume or more per 1 minute, the percentage of the organic phase in the entire mobile phase at the end of step 2 is 35 to 60% by volume, and related substance 6 is detected.

The method more preferably satisfies the following requirements in steps 1 and 2, wherein the organic phase in the mobile phase contains acetonitrile, the aqueous phase contains water, and the mobile phase contains sodium dihydrogen phosphate.
Step 1: the percentage of the organic phase in the entire mobile phase is 3 to 7% by volume, the operation mode is isocratic, the measurement time is 15 to 28 minutes, and related substances 1 to 5 are detected:
Step 2: after step 1, elution is performed by applying a gradient of increasing the percentage of the organic phase in the entire mobile phase by 0.9% by volume or more per 1 minute, the percentage of the organic phase in the entire mobile phase at the end of step 2 is 35 to 60% by volume, the measurement time is 10 to 50 minutes, and related substance 6 is detected.

The method more preferably satisfies the following requirements in steps 1 and 2, wherein the organic phase in the mobile phase contains acetonitrile, the aqueous phase contains water, and the mobile phase contains sodium dihydrogen phosphate.
Step 1: the percentage of the organic phase in the entire mobile phase is 3 to 7% by volume, the operation mode is isocratic, the measurement time is 15 to 28 minutes, and related substances 1 to 5 are detected:
Step 2: after step 1, elution is performed by applying a gradient of increasing the percentage of the organic phase in the entire mobile phase by 0.9% by volume or more per 1 minute, the percentage of the organic phase in the entire mobile phase at the end of step 2 is 35 to 60% by volume, the measurement time is 10 to 50 minutes, the flow rate at the end of step 2 is 1.0 to 1.5 times the flow rate in step 1, and related substance 6 is detected.

The method more preferably satisfies the following requirements in steps 1 and 2, wherein the organic phase in the mobile phase contains acetonitrile, the aqueous phase contains water, and the mobile phase contains methanol and sodium dihydrogen phosphate:
Step 1: the percentage of the organic phase in the entire mobile phase is 3 to 7% by volume, the operation mode is isocratic, the measurement time is 15 to 28 minutes, and related substances 1 to 5 are detected.
Step 2: after step 1, elution is performed by applying a gradient of increasing the percentage of the organic phase in the entire mobile phase by 0.9% by volume or more per 1 minute, the percentage of the organic phase in the entire mobile phase at the end of step 2 is 35 to 60% by volume, the measurement time is 10 to 50 minutes, the flow rate at the end of step 2 is 1.0 to 1.5 times the flow rate in step 1, and related substance 6 is detected.

EXAMPLES

Measurement was performed by high-performance liquid chromatography under the following test conditions.

Detector: Ultraviolet spectrophotometer (wavelength: 210 nm).
Column: An octadecylsilyl silica gel column for liquid chromatography (3 µm or 5 µm) was placed in a stainless steel column with an inner diameter of 4.6 mm and a length of 15 cm.
Column temperature: 40° C.
Flow rate: stated in each Example.
Mobile phase: stated in each Example.
Gradient: stated in each Example.

The samples to be measured by high-performance liquid chromatography were prepared as follows.

Trifluridine was dissolved in a solution having the same composition as that of a mobile phase to be used under each of the measurement conditions, and the resulting product was suitably diluted so that the trifluridine concentration was about 0.8 mg/mL, thus obtaining samples.

In each Example, the expression "%" in each mobile phase refers to % by volume.

Example 1-1

Column: Hydrosphere C18, produced by YMC Co., Ltd. (3 µm)
Flow rate: 1.0 mL/min
Mobile phase A: An aqueous solution of 0.05 mol/L sodium dihydrogen phosphate
Mobile phase B: Acetonitrile
Gradient: The mobile phase A and the mobile phase B were controlled by varying the concentrations as follows:
0 to 18 minutes: 95% A/5% B,
18 to 55 minutes: 95% A/5% B→60% A/40% B,
55 to 55.1 minutes: 60% A/40% B→95% A/5% B,
after 55.1 minutes: 95% A/5% B FIG. 1 shows the measurement results. The results confirmed that the retention time of trifluridine was 17.2 minutes. The results according to this measurement method confirmed that trifluridine did not overlap with valleys or ghost peaks in the baseline.

Example 1-2

Gradient: The mobile phase A and the mobile phase B were controlled by varying the concentrations as follows:
0 to 18 minutes: 95% A/5% B,
18 to 48 minutes: 95% A/5% B→60% A/40% B,
48 to 48.1 minutes: 60% A/40% B→95% A/5% B,
after 48.1 minutes: 95% A/5% B The conditions of the column, the flow rate, the mobile phase A, and the mobile phase B were the same as in Example 1.

The results according to this measurement confirmed that trifluridine did not overlap with ghost peaks.

Example 1-3

Gradient: The mobile phase A and the mobile phase B were controlled by varying the concentrations as follows:
0 to 20 minutes: 95% A/5% B
20 to 50 minutes: 95% A/5% B→60% A/40% B,
50 to 50.1 minutes: 60% A/40% B→95% A/5% B,
after 50.1 minutes: 95% A/5% B The conditions of the column, the flow rate, the mobile phase A, and the mobile phase B were the same as in Example 1.

Figure 2:
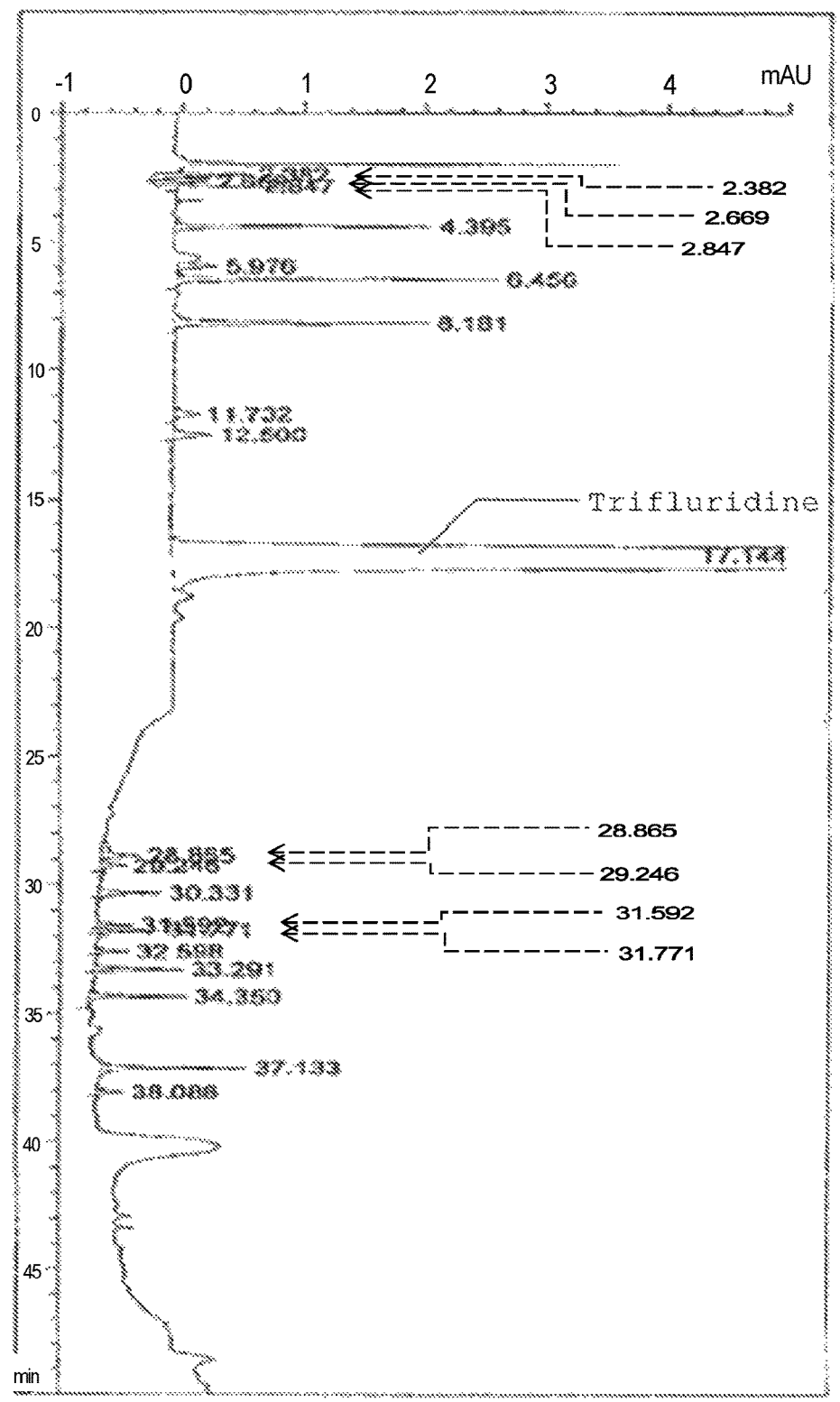
FIG. 2 shows the chromatogram obtained in Example 1-3.

FIG. 2 shows the measurement results. The results confirmed that the retention time of trifluridine was 17.1 minutes. The results according to this measurement method confirmed that trifluridine did not overlap with valleys or ghost peaks in the baseline.

Example 1-3-1

Gradient: The mobile phase A and the mobile phase B were controlled by varying the concentrations as follows:
0 to 15 minutes: 95% A/5% B
15 to 45 minutes: 95% A/5% B→60% A/40% B,
45 to 45.1 minutes: 60% A/40% B→95% A/5% B,
after 45.1 minutes: 95% A/5% B The conditions of the column, the flow rate, the mobile phase A, and the mobile phase B were the same as in Example 1.

Column: Inertsil ODS-3, produced by GL Sciences Inc. (3 µm)

The conditions of the flow rate, the mobile phase A, and the mobile phase B were the same as in Example 1-3.

The results according to this measurement confirmed that trifluridine did not overlap with ghost peaks.

Example 1-3-2

Column: Inertsil ODS-4, produced by GL Sciences Inc. (3 µm)

The conditions of the flow rate, the mobile phase A, the mobile phase B, and the gradient were the same as in Example 1-3-1.

The results according to this measurement confirmed that trifluridine did not overlap with ghost peaks.

Example 1-3-3

Column: YMC-Pack Pro C18 RS (3 µm)
The conditions of the flow rate, the mobile phase A, the mobile phase B, and the gradient were the same as in Example 1-3-1.

The results according to this measurement confirmed that trifluridine did not overlap with ghost peaks.

Example 1-3-4

Column: YMC-Pack Pro C18 (3 µm)
The conditions of the flow rate, the mobile phase A, the mobile phase B, and the gradient were the same as in Example 1-3-1.

The results according to this measurement confirmed that trifluridine did not overlap with ghost peaks.

Example 2-1

Column: Hydrosphere C18, produced by YMC (5 µm)
Flow rate: 0 to 21 minutes: 1.0 mL/min, 21 to 46 minutes: 1.0→1.3 mL/min, 46 to 46.1 minutes: 1.3→1.0 mL/min, after 46.1 minute: 1.0 mL/min
Mobile phase A: Sodium dihydrogenphosphate dihydrate (3.0 g) was dissolved in water (1000 mL), and phosphoric acid was added to the resulting mixture to adjust the pH to 2.2, followed by the addition of methanol (10 mL).

Figure 3:
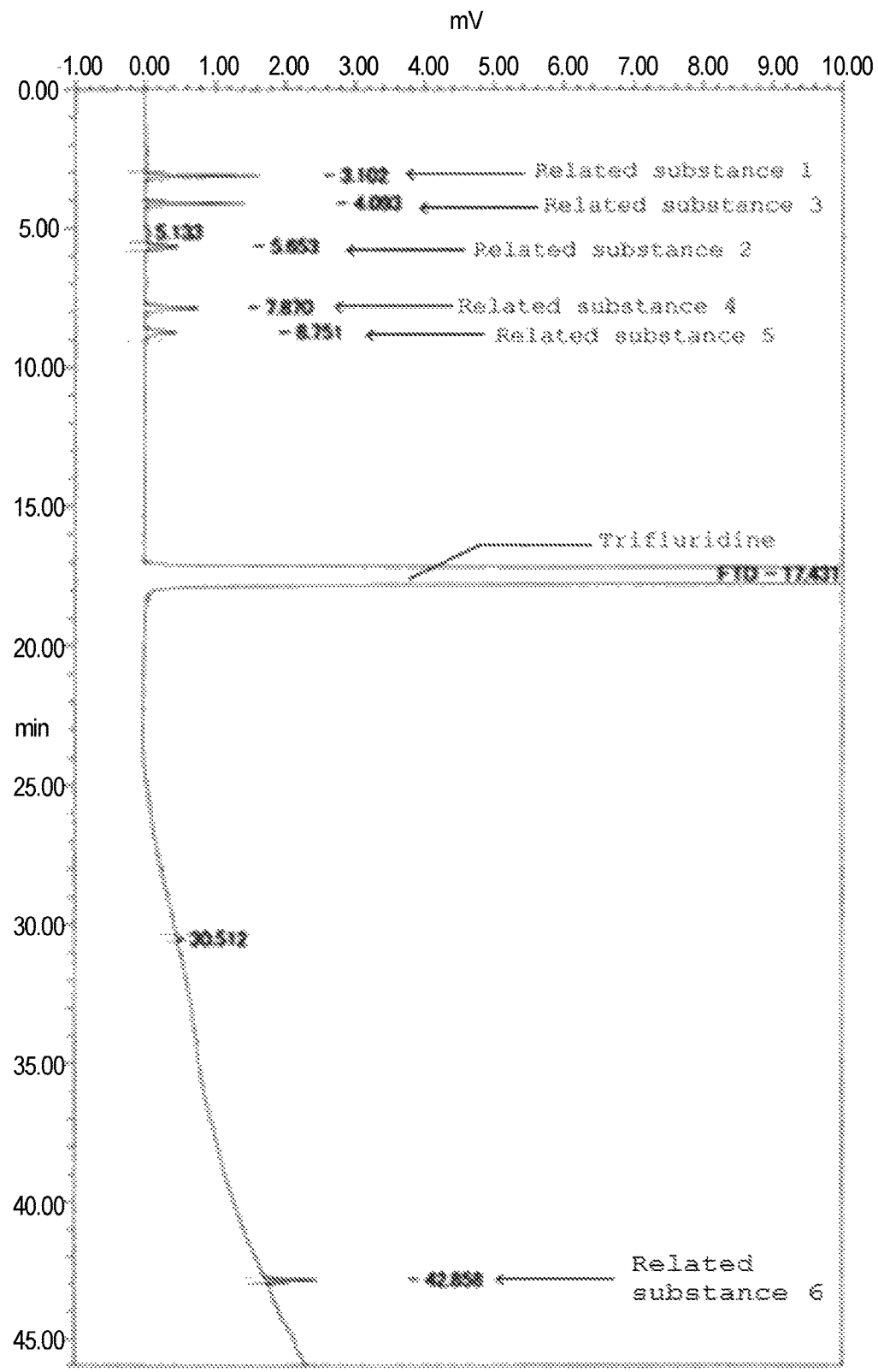
FIG. 3 shows the chromatogram obtained in Example 2-1.

Mobile phase B: Acetonitrile
Gradient: The mobile phase A and the mobile phase B were controlled by varying the concentrations as follows:
0 to 21 minutes: 96% A/4% B,
21 to 46 minutes: 96% A/4% B→45% A/55% B,
46 to 46.1 minutes: 45% A/55% B→96% A/4% B
after 46.1 minutes: 96% A/4% B FIG. 3 shows the measurement results. The results confirmed that the retention time of trifluridine was 17.4 minutes. Further, the retention time of related substance 1 was confirmed to be 3.1 minutes, the retention time of related substance 2 was confirmed to be 5.6 minutes, the retention time of related substance 3 was confirmed to be 4.1 minutes, the retention time of related substance 4 was confirmed to be 7.9 minutes, the retention time of related substance 5 was confirmed to be 8.8 minutes, and the retention time of related substance 6 was confirmed to be 42.9 minutes.

The retention time of each of the related substances detected here was consistent with the retention time of each related substance separately purchased or synthesized, which confirmed that the related substances detected here were compounds having the structures of related substances 1 to 6.

In conclusion, the results according to this measurement method confirmed that trifluridine did not overlap with valleys or ghost peaks in the baseline. The results also confirmed that it was possible to separate each trifluridine-related substance from trifluridine. Furthermore, the peak of related substance 6 was consistent with the retention time of related substance 6 synthesized below. In view of this, the peak at retention time of 42.9 minutes in this measurement was considered to represent related substance 6.

Example 2-2

Column: Unison UK-C18, produced by Imtakt Co p. (5 μm)
The other conditions were the same as in Example 2-1. The conclusion in regard to this measurement was the same as that of Example 2-1.

Example 2-3

Mobile phase A: Sodium dihydrogenphosphate dihydrate (3.0 g) was dissolved in water (1000 mL), and phosphoric acid was added to the resulting mixture to adjust the pH to 2.2, followed by the addition of methanol (9 mL).
The other conditions were the same as in Example 2-1.
The conclusion in regard to this measurement was the same as that of Example 2-1.

Example 2-4

Flow rate: 0 to 21 minutes: 0.95 mL/min, 21 to 46 minutes: 0.95→1.25 mL/min, 46 to 46.1 minutes: 1.25→0.95 mL/min, after 46.1 minutes: 0.95 mL/min
The other conditions were the same as in Example 2-1.
The conclusion in regard to this measurement was the same as that of Example 2-1.

Example 2-5

Gradient: The mobile phase A and the mobile phase B were controlled by varying the concentrations as follows:
0 to 21 minutes: 95.8% A/4.2% B
21 to 46 minutes: 95.8% A/4.2% B→43% A/57% B
46 to 46.1 minutes: 43% A/57% B→95.8% A/4.2% B
after 46.1 minutes: 95.8% A/4.2% B
The other conditions were the same as in Example 2-1.
The conclusion in regard to this measurement was the same as that of Example 2-1.

Example 3

Column: Inertsil ODS-2, produced by GL Sciences Inc. (5 μm)
Flow rate: 1.0 mL/min
Mobile phase A: An aqueous solution of 0.05 mol/L sodium dihydrogenphosphate
Mobile phase B: Acetonitrile
Gradient: The mobile phase A and the mobile phase B were controlled by varying the concentrations as follows:
0 to 2 minutes: 85% A/15% B
2 to 7 minutes: 85% A/15% B→60% A/40% B
after 7 minutes: 60% A/40% B The measurement results confirmed that the retention time of trifluridine was 3.6 minutes. Further, the retention times of related substances 1 to 5 overlapped with each other within a range of 1.0 to 2.5 minutes, and the peak areas of these substances could not be calculated. In conclusion, according to this measurement method, although the detection of trifluridine-related substances 1 to 5 was not necessarily accurate, the detection of related substance 6 was possible.

Example 4

Column: Inertsil ODS-2, produced by GL Sciences Inc. (5 μm)
Flow rate: 1.0 mL/min
Mobile phase A: Water
Mobile phase B: Acetonitrile
Gradient: Isocratic at 60% A/40% B The measurement results confirmed that the retention time of trifluridine was 1.8 minutes, and the retention time of related substance 6 was 7.6 minutes. Although the retention times of related substances 1 to 5 overlapped with each other within a range of 1.6 to 2.5 minutes, and the peak areas of these substances could not be calculated, the detection of related substance 6 was possible.

Reference Example

Synthesis of 5'-(4-chlorophenylcarboxy)-2'-deoxy-5-trifluoromethyluridine (Related Substance 6)

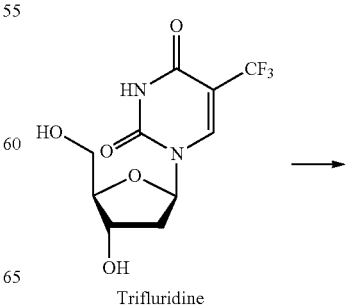

Trifluridine

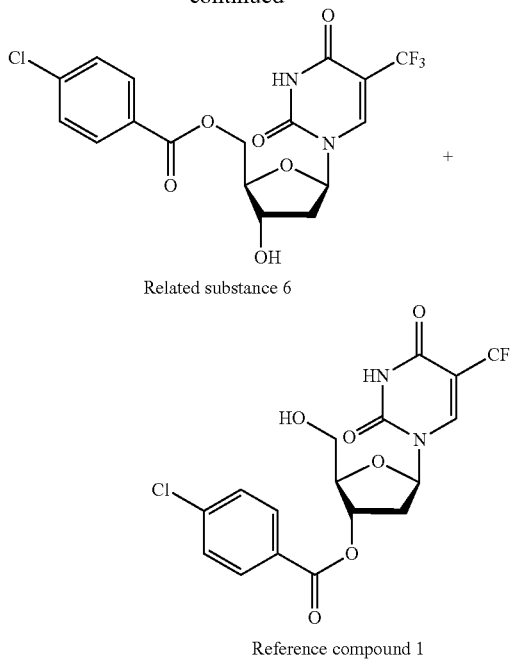

Related substance 6

Reference compound 1

Commercially available trifluridine (2.00 g) was dissolved in pyridine (8 mL), and p-chlorobenzoylchloride (1.18 g) was slowly added thereto in an ice bath, followed by stirring at room temperature for 1 hour. Thereafter, the solvent was distilled off, and the residue was purified by silica gel column chromatography (chloroform/methanol=100/0 to 91/9) to yield 5T-(4-chlorophenylcarboxy)-2'-deoxy-5-trifluoromethyluridine (1.49 g, related substance 6) and 3'-(4-chlorophenylcarboxy)-2'-deoxy-5-trifluoromethyluridine (238 mg, reference compound 1).

Related substance 6: 1H-NMR (DMSO-d6, 270 MHz) δ (ppm) 11.91 (1H, s), 8.03 (1H, s), 7.95 (2H, d, J=6.75 Hz), 7.60 (2H, d, J=6.75 Hz), 6.07 (1H, t, J=6.55 Hz), 5.48 (1H, d, J=4.29 Hz), 4.56-4.38 (3H, m), 4.18-4.16 (1H, m)

Reference compound 1: 1H-NMR (DMSO-d6, 270 MHz) δ (ppm) 11.92 (1H, s), 8.72 (1H, s), 8.03 (2H, d, J=8.07 Hz), 7.63 (2H, d, J=8.07 Hz), 6.27 (1H, t, J=6.75 Hz), 5.48-5.42 (2H, m), 4.28 (1H, s) 3.72 (2H, s).

The invention claimed is:

1. A method for detection, comprising:
    subjecting a sample including trifluridine or a salt thereof to high-performance liquid chromatography with a mobile phase comprising an organic phase and an aqueous phase; and
    detecting related substance 6 and at least one of related substances 1 to 5 in the sample by the high-performance liquid chromatography,
    wherein the high-performance liquid chromatography comprises steps 1 and 2, step 1 is conducted with the mobile phase including the organic phase in a range of from 1 to 14% by volume, step 2 is conducted after step 1 and includes performing elution by applying a gradient of increasing the percentage of the organic phase in the mobile phase,
    the organic phase comprises at least one solvent and optionally 10% or less water,
    the aqueous phase comprises water and optionally 10% or less of at least one solvent,
    at least one of the related substances 1 to 5 is detected in the mobile phase of step 1, and
    the related substance 6 is detected in the mobile phase of step 2,
    where the related substances 1 to 6 are as follows:
    related substance 1: 5-carboxyuracil,
    related substance 2: 5-carboxy-2'-deoxy-uridine,
    related substance 3: 2'-deoxy-5-methoxycarbonyluridine,
    related substance 4: trifluorothymine,
    related substance 5: 5-methoxycarbonyluracil, and
    related substance 6: 5'-(4-chlorophenylcarboxy)-2'-deoxy-5-trifluoromethyluridine.

2. The method according to claim 1, wherein the organic phase is acetonitrile.

3. The method according to claim 1, wherein the aqueous phase includes phosphate.

4. The method according to claim 1, wherein the aqueous phase includes methanol.

5. The method according to claim 1, wherein step 1 is performed under isocratic conditions.

6. The method according to claim 1, wherein, in step 1, the percentage of the organic phase in the mobile phase is within a range of 2 to 10% by volume.

7. The method according to claim 1, wherein, in step 1, the percentage of the organic phase in the mobile phase is within a range of 3 to 7% by volume.

8. The method according to claim 1, wherein the percentage of the organic phase in the mobile phase at the end of step 2 is within a range of 25 to 70% by volume.

9. The method according to claim 1, wherein the percentage of the organic phase in the mobile phase at the end of step 2 is within a range of 30 to 65% by volume.

10. The method according to claim 1, wherein the percentage of the organic phase in the mobile phase at the end of step 2 is within a range of 35 to 60% by volume.

11. The method according to claim 1, wherein, in step 2, the elution is performed by applying a gradient of increasing the percentage of the organic phase in the mobile phase by 0.9% by volume or more per 1 minute.

12. The method according to claim 1, wherein, in step 2, the elution is performed by applying a gradient of increasing the percentage of the organic phase in the mobile phase by 1.0% by volume or more per 1 minute.

13. The method according to claim 1, wherein, in step 2, the elution is performed by applying a gradient of increasing the percentage of the organic phase in the mobile phase by 2.0% by volume or more per 1 minute.

14. The method according to claim 1, wherein, in step 2, the elution is performed by applying a gradient of increasing the percentage of the organic phase in the mobile phase by 2.0% by volume or more and 5.0% by volume or less per 1 minute.

15. The method according to claim 1, wherein step 2 has a measurement time within a range of 10 to 50 minutes.

16. The method according to claim 1, wherein a flow rate at the end of step 2 is 1.0 to 1.5 times a flow rate in step 1.

17. A quality control method of a combination drug including trifluridine, comprising:
    performing the method of claim 1, wherein the sample is the combination drug.

18. A method of detecting impurities in a combination drug including trifluridine, comprising:
    performing the method of claim 1, wherein the sample is the combination drug.

* * * * *